Jan. 13, 1959 E. S. BOERNER Plant Pat. 1,799
ROSE PLANT
Filed June 3, 1958
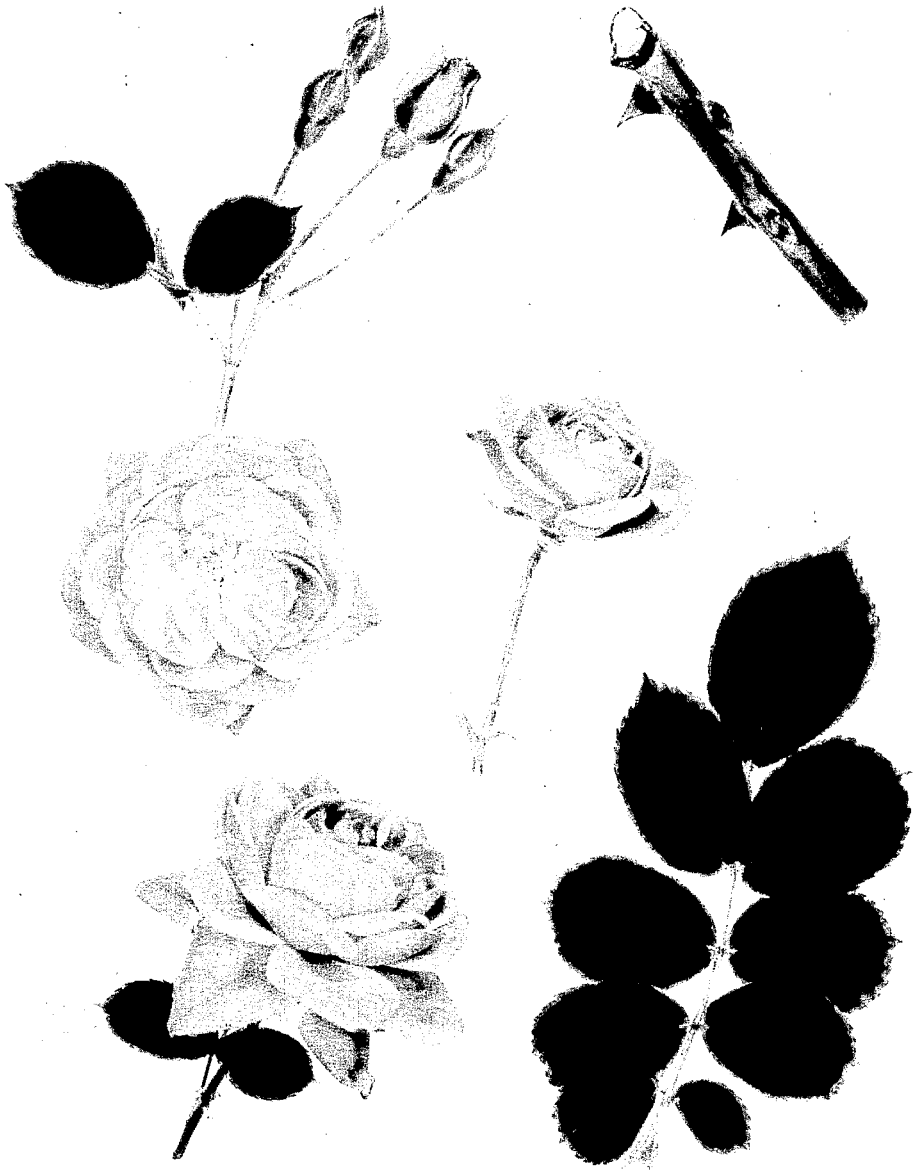
Inventor.
E. S. Boerner
By: Robb & Robb
Attorneys United States Patent Office Plant Pat. 1,799
Patented Jan. 13, 1959

1,799

ROSE PLANT

Eugene S. Boerner, Newark, N. Y., assignor to Jackson & Perkins Company, Newark, N. Y., a corporation of New York Application June 3, 1958, Serial No. 739,642

1 Claim. (Cl. 47—61)

The present invention relates to a new and distinct variety of rose plant of the large-flowered polyantha class, which was originated by me by crossing an unnamed and unpatented orange-red seedling with the variety "Independence" (Plant Patent No. 1,036).

The primary objective of this breeding was to produce a new rose variety that is suitable for use by florists for pot forcing. This objective was fully achieved, along with other desirable features, as evidenced by the following unique combination of characteristics which are outstanding in the new variety and distinguish it from its parents, as well as from all other varieties of which I am aware:

(1) Medium size, upright and compact habits of plant growth;

(2) Irregular flower cluster habit;

(3) A distinctive Spectrum Red, lightly overcast with Scarlet Red, general color tonality of the flowers;

(4) Long-lasting quality of the flower color; and (5) Suitability for pot forcing use by florists.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed orange-red seedling.
*Pollen parent.*—"Independence."
Classification:
*Botanic.*—Large-flowered polyantha.
*Commercial.*—Floribunda.

*Flower*

(Observations made from specimens grown in a greenhouse at Newark, New York, near mid-morning in the early part of April.)

Blooming habit: Recurrent—continuous.
Bud:
*Size.*—Medium.
*Form.*—Ovoid; is not affected by wet or hot weather.
*Color.*—When sepals first divide—Oxblood Red, Plate 1. When petals begin to unfurl—Carmine, Plate 1. When half-blown: inside of petals—Spectrum Red, Plate 1, with lower half of petal lightly overcast with Rose Red, Plate 12; reverse of petals—Carmine, Plate 1, lightly overcast with Spectrum Red, Plate 1.

*Sepals.*—Slightly branched; curl back when petals begin to unfurl. Color: inside—Absinthe Green, Plate 31; outside—Light Cress Green, Plate 31.
*Calyx.*—Color—Biscay Green, Plate 17. Shape—pear. Size—small. Aspect—smooth. Odor when rubbed—none.
*Peduncle.* — Length — medium. Aspect — rough. Strength — erect; slender. Color — Malachite Green, Plate 32.
*Opening.*—Opens up well; is not affected by adverse weather conditions.
Bloom:
*Size.*—Small. Average size when fully expanded—2 inches.
*Borne.*—In irregular clusters which fully cover plant.
*Stems.*—Medium length; strong.
*Form (when first open).*—Cupped. Permanence—retains its form to the end.
*Petalage.*—Double (full but open center). Number of petals under normal conditions, 50.
*Color.*—Center of flower—Scarlet Red, Plate 1. Outer petals—Spectrum Red, Plate 1, lightly overcast with Carmine, Plate 1 on the outer edge of the petal. Base of petals (aiglet)—Sulphur Yellow, Plate 5. Inside of petals—Spectrum Red, Plate 1, lightly overcast with Scarlet Red, Plate 1. Reverse of petals—Spectrum Red, Plate 1, lightly overcast with Rose Red, Plate 12. General tonality from a distance—Spectrum Red, Plate 1, lightly overcast with Scarlet Red, Plate 1.
*Discoloration.*—General tonality at end of first day—Spectrum Red, Plate 1, lightly overcast with Scarlet Red, Plate 1. Second day—Spectrum Red, Plate 1, lightly overcast with Scarlet Red, Plate 1. Third day—Scarlet Red, Plate 1.
Petals:
*Texture.*—Thick; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Medium size; many; regularly arranged around styles. Color—Mikado Orange, Plate 3.
Stamens, filaments (threads): Medium length. Color—Light Green-Yellow, Plate 5.
Pollen: Color—Capucine Buff, Plate 3.
Styles: Bunched; uneven length; medium length; thin.
Stigmas: Color—Light Turtle Green, Plate 32.
Ovaries: All enclosed in calyx.
Hips: None.
Seeds: None.

*Plant*

Form: Bush.
Growth: Medium; upright; compact.
Foliage: Compound of 3–9 leaflets.
*Size.*—Medium.
*Quantity.*—Abundant.
*Color.*—New foliage: upper side—Yew Green, Plate 31; under side—Light Bice Green, Plate 17. Old foliage: upper side—Varley's Green, Plate 17; under side—Light Elm Green, Plate 17.
*Shape.*—Oval pointed.
*Texture.*—Upper side—glossy. Under side—smooth.

*Ribs and veins.*—Ordinary.
*Edge.*—Serrated (saw-toothed).
*Serration.*—Both double and single; small.
*Leaf stem.*—Color—Absinthe Green, Plate 31. Under side—prickly.
*Stipules.*—Medium length; smooth.

Wood:
*New wood.*—Color—Chromium Green, Plate 32. Bark—smooth.
*Old wood.*—Color—Cress Green, Plate 31. Bark—smooth.

Thorns:
*Thorns.*—Quantity: on main stalks from base—ordinary; on laterals from stalk — ordinary. Form—narrow base; short; hooked downward. Color (when young)—Begonia Rose, Plate 1. Position—irregular.

*Prickles.*—Quantity: on main stalks—none; on laterals—none.
*Short needles.*—Quantity: on main stalks—none; on laterals—none.

I claim:

A new and distinct variety of rose plant of the large-flowered polyantha class, substantially as herein shown and described, characterized particularly as to novelty by the unique combination of medium size, upright and compact habits of plant growth, irregular flower cluster habit, a distinctive Spectrum Red, lightly overcast with Scarlet Red, general color tonality of the flowers, long-lasting quality of the flower color, and a suitability for pot forcing use by florists.

No references cited.